United States Patent
Woltering et al.

(10) Patent No.: US 6,893,812 B2
(45) Date of Patent: May 17, 2005

(54) THREE-DIMENSIONAL EX VIVO ANGIOGENESIS SYSTEM

(75) Inventors: Eugene A. Woltering, Kenner, LA (US); Seza A. Gulec, New Orleans, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/866,296

(22) Filed: May 25, 2001

(65) Prior Publication Data

US 2002/0177121 A1 Nov. 28, 2002

Related U.S. Application Data

(60) Provisional application No. 60/325,758, filed on May 30, 2000.

(51) Int. Cl.$^7$ .......................... C12Q 1/00; C12N 1/00; C12N 1/02; C12N 5/06; C12N 5/08
(52) U.S. Cl. ............................. 435/4; 435/1.1; 435/29; 435/325; 435/375; 435/395
(58) Field of Search .............................. 435/4, 1.1, 29, 435/325, 375, 395, 25, 28, 525

(56) References Cited

U.S. PATENT DOCUMENTS

| | | | |
|---|---|---|---|
| 5,616,478 A | * 4/1997 | Chetverin et al. | 435/91.2 |
| 5,856,184 A | * 1/1999 | Sarras et al. | 435/363 |
| 5,976,782 A | 11/1999 | Parish et al. | 435/4 |
| 6,465,613 B1 | 10/2002 | Coy et al. | 530/311 |

OTHER PUBLICATIONS

Barendsz–Janson et al. Journal of Vascular Research. 1998, 35:109–114.*
Guyton A. Textbook of Medical Physiology. 1991. 8 edition. W.B. Sauders Company. p. 190.*
Brown et al. Laboratory Investigation. 1996. vol. 75, No. 4, pp. 539–555.*
Montesano et al. Cell Biology International Reports. 1985. vol. 9, No. 10, pp. 869–875.*
Lugasy et al. C R Acad Sci Ser III Sci Vie. (1991), 313 (1), 37–44.*
Gulec, S. et al., "Antitumor and antiangiogenic effects of somatostatin receptor–targeted in situ radiation with $^{111}$In–DTPA–JIC 2DL," J. Surg. Res. vol. 97, pp. 131–137 (2001).
Knott, R.M. et al., "A Model System for Study of Human Retinal Angiogenesis: Activation of Monocytes and Endothelial Cells and the Association with the Expression of the Monocarboxylate Transporter Type 1 (MCT–1)," Diabetologia, vol. 42, pp. 870–877 (1999).

* cited by examiner

*Primary Examiner*—Vera Afremova
(74) *Attorney, Agent, or Firm*—John H. Runnels

(57) ABSTRACT

An in vitro tissue angiogenesis and vasculogenesis system is disclosed that allows the outgrowth of microvessels from a three-dimensional tissue fragment implanted in a matrix. The matrix may, for example, be a fibrin- or collagen-based matrix fed by a growth medium, for example, a mixture of tissue culture medium, serum, or a layer of growth medium containing a defined mixture of growth factors. This system, which may be used with human or other mammalian or animal tissues, may be used in assaying tumor angiogenic potential, or in promoting angiogenesis in other tissues, e.g., promoting angiogenesis prior to transplantation of a tissue. The angiogenic potential of a tissue can be determined by measuring the growth of microvessels into the matrix. The three-dimensional structure of the tumor or other tissue is maintained in the matrix, including blood vessels. In another aspect, the method allows for the proliferation of a tissue specimen, thus increasing the mass of cells available for subsequent transplant; and the method also provides for the proliferation of blood vessels from the tissue mass, thus enhancing the chance of successful engraftment.

13 Claims, No Drawings

THREE-DIMENSIONAL EX VIVO ANGIOGENESIS SYSTEM

The benefit of the May 30, 2000 filing date of provisional application 60/325,758 is claimed under 35 U.S.C. §119(e).

The development of this invention was subject to a contract between the Board of Supervisors of Louisiana State University and Agricultural and Mechanical College, and the United States Department of Veterans Affairs. The Government has certain rights in this invention.

This invention pertains to methods to promote ex vivo angiogenesis in tissues, for example, in tissues to be transplanted. This invention also pertains to methods to assay angiogenesis in tissues, for example tumor tissues, and to assess the effects of inducers and inhibitors of angiogenesis. Such information can be of use, for example, in making a prognosis for a tumor, or in evaluating the likely effect in vivo of anti-angiogenic factors on a tumor.

"Neovascularization," "vasculogenesis," and "angiogenesis" are terms that describe the formation of new capillaries. Angiogenesis is a normal physiological process, the generation of new capillary blood vessels from pre-existing vessels. Angiogenesis rarely occurs in physiologically normal adult tissues. Exceptions include the ovary, the endometrium, the placenta, wound healing, and inflammation. Angiogenesis is an important step in ovulation and also in implantation of the blastula after fertilization. Angiogenesis is sometimes distinguished from vasculogenesis, the emergence of blood vessels de novo from a subpopulation of mesenchymal cells known as angioblasts, which differentiate into endothelial cells.

The identification of several angiogenic factors and the isolation and culture of capillary endothelial cells (ECs) have led to a greater understanding of the cellular and biochemical bases of new vessel growth. Until recently ECs have been the focus of most studies of microvascular growth. However, capillaries are not simply tubes of ECs; they also contain a second cellular component, the mural cell, or pericyte. Angiogenesis involves the differential growth and sprouting of endothelial tubes, and the recruitment and differentiation of mesenchymal cells into vesicular smooth muscle cells and pericytes. Communication between the endothelium and the mesenchyme is important for angiogenesis. Three such communication pathways have been identified:

(1) Mesenchymal cells signal endothelial cells via the angiopoietin/Tie-2 signaling pathway. See Suri et al., Cell 87: 1171 (1996); T. Sato et al. Nature 376, 7074 (1995); Maisonpierre et al., Science 277: 55 (1997).

(2) Endothelial cells induce differentiation of pericytes through the platelet-derived growth factor (PDGF) signaling pathway. See Lindahl et al. Science 277: 242 (1997); Soriano, Genes Dev. 8: 1888 (1994).

(3) An endoglin-mediated pathway of endothelial-mesenchymal communication was reported by Li et al. Science. 284: 1534–1537 (1999).

In normal adult mammals, angiogenesis occurs infrequently, yet it can be rapidly induced in response to various stimuli. The normal rate of capillary endothelial cell turnover in adult mammals is typically measured in months or years. However, when the normally quiescent endothelial cells lining venules are stimulated, they will degrade their basement membrane and proximal extracellular matrix, migrate directionally, divide, and organize into new functioning capillaries with new basal lamina within a matter of days. This dramatic amplification of the microvasculature of a tissue is temporary, for as rapidly as they are formed the new capillaries virtually disappear, returning the tissue's vasculature to its previous state.

Among the most extensively studied of normal angiogenic processes is wound repair. Important characteristics of wound-associated angiogenesis are that it is local, rapid, transient, tightly controlled, and that it promptly regresses back to a steady-state level. The abrupt termination of angiogenesis following wound repair apparently results from two control mechanisms, mechanisms that are not mutually exclusive. First, due to factors that are not well understood, there appears to be a marked reduction in the synthesis or elaboration of angiogenic mediators. Second, there appears to be a simultaneous increase in levels of substances that inhibit new vessel growth. The control of angiogenesis thus depends on a balance of several positive and negative regulators.

Recent research has begun to uncover the genetic mechanisms controlling angiogenesis. See Maswell et al. Nature 399, 271–275 (1999); Stebbins et al., Science 284, 455–461 (1999); Kaumra et al. Science 284, 662–665.

Angiogenesis is regulated by both angiogenic and angiostatic factors. The role of inhibitors in angiogenesis was first suggested by observations that hyaline cartilage appeared to be particularly resistant to vascular invasion. It was later observed that many other cell and tissue extracts also contain inhibitors of angiogenesis. Several natural and artificial angiogenic inhibitors have been identified, including: inhibitors of basement membrane biosynthesis, placental RNase inhibitor, lymphotoxin, interferons, prostaglandin synthetase inhibitors, heparin-binding fragments of fibronectin, protamine, angiostatic steroids, several anti-neoplastic and anti-inflammatory agents, platelet factor-4, thrombospondin-1, angiostatin, integrin antagonists, and certain forms of thrombin.

Gasparini, Drugs Jul; 58(1):17–38(1999) discusses the possible use of angiogenesis inhibitors to intervene into neoplastic processes. The basic idea is to use inhibitory agents to block angiogenesis, thereby causing tumor regression in various types of neoplasia. Therapeutic candidates include naturally occurring angiogenesis inhibitors (e.g., angiostatin, endostatin, platelet factor-4), specific inhibitors of endothelial cell growth (e.g., TNP-470, thalidomide, interleukin-12), agents that neutralize angiogenic peptides (e.g., antibodies to fibroblast growth factor or vascular endothelial growth factor, suramin and its analogs, tecogalan, agents that neutralize receptors for angiogenic factors, agents that interfere with vascular basement membrane and extracellular matrix (e.g., metalloprotease inhibitors, angiostatic steroids), and anti-adhesion molecules (e.g., antibodies such as anti-integrin alpha v beta 3). Rosen L, Oncologist; 5 Suppl 1:20–7 (2000) discusses strategies for the application of antiangiogenic therapies to cancer.

Other compounds that have been described as inhibitors of angiogenesis include the cartilage-derived inhibitor TIMP, thrombospondin, laminin peptides, heparin/cortisone, minocycline, fumagillin, difluoromethyl ornithine, and sulfated chitin derivatives.

Of particular interest is the new class of antiangiogenic substances called METH proteins. Their enzymatic activity makes this class of agents candidates for possible control by small molecules, a goal that has eluded pharmacotherapy. See Vazquez F. et al. J Biol Chem August 13;274(33):23349–57 (1999). The angiotensin II type 2 receptor is another example of a receptor that mediates an antiangiogenic response, and that may be amenable to regulation by small molecules.

Hypoxic conditions can induce angiogenesis. Conversely, when newly-formed vessels bring oxygen to the tissue, the proteins involved in induction of angiogenesis are marked for destruction and angiogenesis ceases.

Numerous factors have also been identified that induce vessel formation in vitro or in vivo in animal models. These include: αFGF, βFGF, TGF-α, TNF-α, VPF, VEGF, PDGF, monobutyrin, angiotropin, angiogenin, hyaluronic acid degradation products, and AGE-products.

Monitoring angiogenic processes can provide valuable information on tumor progression, metastasis and prognosis (Szabo and Sandor, Eur J Surg Suppl;(582):99–103 (1998)). There is an unfilled need for improved methods of monitoring angiogenesis to support the development and application of antiangiogenic interventions. The ability to monitor angiogenesis will also assist the discovery of new antiangiogenic agents.

Diseases Associated with Angiogenesis.

Abnormal angiogenesis occurs when improper control of angiogenesis causes either excessive or insufficient blood vessel growth. For example, conditions such as ulcers, strokes, and heart attacks may result in some cases from levels of angiogenesis insufficient for normal healing. Conversely, excessive blood vessel proliferation may favor tumor growth and spread, blindness, and arthritis. Diseases that have been associated with neovascularization include, for example, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme disease, systemic lupus erythematosis, retinopathy of prematurity, Eales disease, Bechets disease, infections causing retinitis or choroiditis, presumed ocular histoplasmosis, Bests disease, myopia, optic pits, Stargarts disease, pars planitis, chronic retinal detachment, hyperviscosity syndrome, toxoplasmosis, trauma, and post-laser complications. Other angiogenic-related diseases may include, for example, diseases associated with rubeosis (neovascularization of the angle), and diseases caused by abnormal proliferation of fibrovascular or fibrous tissue, including all forms of proliferative vitreoretinopathy. An improved ability to monitor angiogenesis can assist in developing improved methods of intervention, diagnosis, and prognosis of such diseases.

Angiogenesis in Solid Tumor Formation and Metastasis.

Angiogenesis is prominent in solid tumor formation and metastasis. Several experimental studies have concluded that primary tumor growth, tumor invasiveness, and metastasis all require neovascularization. The process of tumor growth and metastasis is complex, involving interactions among transformed neoplastic cells, resident tissue cells (e.g., fibroblasts, macrophages, and endothelial cells), and recruited circulating cells (e.g., platelets, neutrophils, monocytes, and lymphocytes). A possible mechanism for the maintenance of tumor growth is an imbalance, or disregulation, of stimulatory and inhibitory growth factors in systems within the tumor. Disregulation of multiple systems allows the perpetuation of tumor growth and eventual metastasis. Angiogenesis is one of many systems that is disregulated in tumor growth. In the past it has been difficult to distinguish between disregulation of angiogenesis and disregulation of other systems affecting a developing tumor. As another complicating factor, Maniotis A J et al. Am J Pathol September; 155(3):739–52 (1999) have noted that aggressive human melanomas mimic vasculogenesis by producing channels of patterned networks of interconnected loops of extracellular matrix, in which red blood cells, but not endothelial cells, are detected. These channels may facilitate perfusion of tumors, independent of perfusion from angiogenesis.

A tumor cannot expand without a blood supply to provide nutrients and remove cellular wastes. Tumors in which angiogenesis is important include solid tumors, and benign tumors including acoustic neuroma, neurofibroma, trachoma and pyogenic granulomas. Inhibiting angiogenesis could halt the growth of these tumors. Angiogenic factors have been reported as being associated with several solid tumors, including rhabdomyosarcoma, retinoblastoma, Ewing sarcoma, neuroblastoma, and osteosarcoma.

Angiogenesis has also been associated with some non-solid tumors, including blood-born tumors such as leukemias, various acute or chronic neoplastic diseases of the bone marrow marked by unrestrained proliferation of white blood cells, usually accompanied by anemia, impaired blood clotting, and enlargement of the lymph nodes, liver, and spleen. It is believed that angiogenesis may play a role in the abnormalities in the bone marrow that give rise to leukemias.

Tumor Growth Beyond 1 to 2 mm Diameter is Dependent on Angiogenesis.

Angiogenesis in normal wound repair appears to be under strict control, and is self-limited. By contrast, neovascularization is exaggerated and is not well-controlled during neoplastic transformation. It appears that tumors continually renew and alter their vascular supply. Normal vascular mass is approximately 20% of total tissue mass, while tumor vascular mass may comprise as much as 50% of the total tumor. Neovascularization is both a marker of pre-neoplastic lesions, as well as a condition that perpetuates tumor growth.

Several studies have found a correlation between the magnitude of tumor-derived angiogenesis and metastasis in melanoma, prostate cancer, breast cancer, and non-small cell lung cancer. These studies support the conclusion that tumor-associated angiogenesis is disregulated, with an imbalance that favors either the expression of local angiogenic factors or the suppression of angiostatic factors. Also, the degree of angiogenic response in a tumor is related to the prognosis; i.e., the higher the degree of angiogenesis, the worse the prognosis.

Experimental Models of Angiogenesis.

A source of angiogenic stimulation can be either endogenous or exogenous to the vessel-sprouting tissue. Exogenous stimulation requires two types of tissue, the stimulating tissue and the responding or sprouting tissue. Endogenous stimulation requires only one tissue, since both the stimulus and the response occur within the same tissue.

Several in vivo angiogenesis models have been developed. The corneal pocket assay involves the surgical implantation of polymer pellets containing angiogenic factors in the cornea of larger animals such as rabbits. Quantitation is difficult, and few such tests have apparently been conducted. The chick chorioallantoic membrane assay involves the removal and transfer of a chick embryo from the shell to a cup. The angiogenic material is suspended in a vehicle, typically a solution of methyl cellulose, and is then dried on a glass cover slip and placed on the chorioallantoic membrane. The appearance of new vessels is observed. The rabbit ear chamber assay requires the surgical insertion of a glass or plastic viewing device, and the measurement of capillary migration by microscopy. However, it is difficult to apply angiogenic materials in this assay. The rat dorsal air sac assay involves implants of stainless steel chambers containing angiogenic factors and is difficult to quantitate. The alginate assay involves the subcutaneous injection into mice of tumor cells encased in alginate.

The endothelial cell proliferation assay relies on measurements of cell proliferation. It is typically performed in 96-well tissue culture plates.

The endothelial cell migration assay assesses migration of endothelial cells toward a stimulus. Inhibition of angiogenesis is shown by blockage of migration in the presence of the inhibitor. See Dameron et al., Science, 265, 1582–84 (1994).

In the endothelial cell tube formation assay, human umbilical vascular endothelial cells (HUVECs) are plated on gels of a matrix such as Matrigel™. See Schnaper et al., J. Cell. Physiol, 156, 235–246 (1993). Matrigel™ is described in U.S. Pat. No. 5,382,514. Baatout S, and Cheta N, Rom J Intern Med 1996 July–December; 34(3–4):263–9 describe Matrigel™ as a mixture of basement membrane proteins including laminin, type IV collagen, entactin/nitrogen and proteoheparan sulfate, and various growth factors. Matrigel™ induces endothelial cells to differentiate, as evidenced both by morphologic changes and by a reduction in proliferation. It therefore offers a convenient system to study biochemical and molecular events associated with angiogenesis. Further, Matrigel™ permits one to study the roles of the extracellular matrix in angiogenesis. Sprouts from vessels in adjacent tissue penetrate into the gel within days of connecting it to the external vasculature.

Maldonado et al., Pathol Oncol Res; 4:225–9 (1998), developed an angiogenesis model that demonstrated that human metastatic prostate cancer cells appeared to induce HUVECs to translocate across a Matrigel-coated membrane.

The corneal micropocket assay is widely accepted as being generally-predictive of clinical usefulness. In this assay, an angiogenic agent is a factor that is seen to consistently act to promote the ingrowth of one or more blood vessels within the cornea, preferably without evidence of the influx of leukocytes.

The rodent mesenteric-window assay is a model that exploits the virtually avascular membranous rodent mesentery. After experimental treatment, angiogenesis is quantified in the mesentery histologically as the number of vessels per unit length of mesentery. See Norrby et al. "Mast-cell-mediated angiogenesis: a novel experimental model"; Virchows Arch B Cell Pathol Incl Mol Pathol; 52:195–206 (1986).

In chemotactic chamber assays, millipore chambers containing tumors are implanted in an animal such as a hamster. Once such device is known as a "Boyden chamber." The Boyden chamber contains an upper well and a blind lower well, separated by a semipermeable membrane. Chemoattractants are placed in the lower well. See, e.g., U.S. Pat. No. 4,912,057.

In the alginate-entrapped tumor cell assay, tumor cells entrapped in alginate are implanted in an animal. See Plunkett and Hailey, Laboratory Investigation, 62:510517 (1990).

In the microbead assay magnetic microbeads are incubated with capillary endothelial cells, such that 10–15 microbeads are internalized per cell. Cells containing the ingested beads are subjected to various stimuli and allowed to proliferate, distributing the ingested beads into daughter cells. Quantification and distribution of the average number of beads in individual cells allows one to monitor endothelial stimulation and inhibition. See Cao Y, et al., Lab Invest August; 78(8):1029–30 (1998).

In a three-dimensional co-culture system, capillary-like structures are induced in a structure containing sandwiched layers of collagen gels and fibrin gels. Each layer can be seeded with cells, such as fibroblasts or cancer cells. It has been reported that in the absence of fibroblasts, endothelial cells do not survive in this system. See Janvier et al. Anticancer Research 17:1551–1558 (1997).

There have also been exogenous models of angiogenesis using serum supplements. Explants of muscular and adipose tissue, minced into small fragments and embedded in a three-dimensional matrix of fibrin or collagen, in the presence of serum, gave rise to an extensive outgrowth of branching and anastomosing capillary-like tubes. See Montesano et al. Cell Biology International Reports, 9:869–875 (1985). This system was not autoregulatory, however, since regulatory substances were provided in the serum.

In each of these assays, tumors are modeled either by the activity of single cells, or of a group of cells that induces the formation of blood vessels originating from tissue exogenous to the implanted tumor, and then penetrating the tumor from without.

Endogenous Angiogenesis Models

By contrast to the exogenous angiogenesis assays described above, endogenous angiogenesis assays have been used to observe whether particular conditions promote the endogenous sprouting of new vessels from tissue into a surrounding cell-free matrix in a serum-free medium.

One endogenous assay is the aortic ring assay. Preexisting blood vessels can generate new vessels in the absence of exogenous angiogenic stimuli, because the vessel wall is autoregulatory through autocrine, paracrine, and juxtacrine mechanisms. ("Juxtacrine" signaling occurs when the ligand and its receptors are both anchored in the cell membrane.) The vessel wall produces growth factors, proteolytic enzymes, matrix components, cell adhesion molecules, and vasoactive factors. Thus, rat aortic or venous explants cultured in collagen gels under serum-free conditions will sprout new vessels induced by the combined effect of injury and exposure to collagen. See Nicosia R F, et al. Int Rev Cytol, 185:1–43 (1999).

Another endogenous angiogenesis assay is the placental explant assay. The endometrium expresses interacting peptide and non-peptide growth factors during endometrial renewal, factors that include epidermal growth factor, transforming growth factors (e.g. TGF-$\beta$), platelet-derived growth factor/thymidine phosphorylase, tumor necrosis factors, and vascular endothelial growth factor (VEGF). See Smith S K, Hum Reprod Update 4:509–19 (1998).

In the angiogenesis assay described by Brown, et al. Lab Invest 75:539–55 (1996), a fragment of human placental blood vessel embedded in a fibrin gel in microculture plates gave rise to a complex network of microvessels during a period of 7 to 21 days in culture. This method is also described in Australian patent AU-B 17500/95. This group has recently published a study of tumor inhibitors using this assay. See Parish et al., Cancer Res; 59: 3433–41 (1999).

Prior Tumor Cell Angiogenesis Models have been Exogenous.

Unlike normal ovary, endometrium, and placenta, most tumor tissue is not specialized to function as an angiogenic organ. Neither does tumor tissue possess autoregulatory angiogenic capacity, as does the aorta. Thus, in all known prior models of tumor angiogenesis, the tumor is an angiogenic stimulus to which the surrounding tissue responds by sprouting new vessels toward and into the tumor. While tumor cell invasion and angiogenesis share several similarities, there are also important differences. The initiation of both processes requires attachment to a basement membrane, followed by disruption of the membrane and migration through the defect. After the invading cell crosses the basement membrane barrier, cell proliferation produces either a new vessel lumen or metastatic foci. It is likely that the two processes are mutually stimulating, since vascularization allows tumor growth, and tumor growth requires vascularization. The two processes operate in opposing directions, however. Tumor cell invasion occurs when cells move from a tumor into surrounding tissue, whereas tumor-induced angiogenesis is the sprouting of new vessels from the surrounding tissue toward the tumor.

Quantitating Angiogenesis.

Several methods have been used to quantitate angiogenesis or perfusion. See, e.g., Hoffman et al., Cancer Res September 1; 57(17): 3847–51 (1997); and Cancer Res September 1;57(17):3847–51 (1997). Okada et al., Jpn J Cancer Res September; 87(9): 952–7 (1996) described the measurement of hemoglobin as a surrogate for direct angiogenesis measurement.

Conrad et al., Lab Invest March; 70(3):426–34 (1994); Iwahana et al., Int. J Exp Pathol 77:109–14 (1996); Rohr et al., Nouv Rev Fr Hematol 34:287–94 (1992); and Nikiforidis et al., Eur J Radiol 29: 168–79 (1999) disclose the use of computer image analysis to quantitate angiogenesis.

Matrices and Extracellular Matrices.

As used in the specification and claims, the term "matrix" refers to a porous, composite, solid or semi-solid substance, for example a gel, having pores or spaces sufficiently large for cells to populate. Depending on context, the term "matrix" can also refer to matrix-forming materials, i.e., materials that will form a matrix under suitable conditions. Matrix-forming materials may, for example, require the addition of a polymerizing agent to form a matrix, e.g., adding thrombin to a solution containing fibrinogen to form a fibrin matrix. Other matrix materials include collagen (all types), combinations of collagen and fibrin, agarose (e.g., Sepharose™), and gelatin.

Extracellular matrices include, for example, collagen, fibrin, fibronectin, and hyaluronic acid. Artificial, biocompatible extracellular matrices include, for example, dextran polymers, polyvinyl chlorides, polyglycolic acids, polylactic acids, polylactic coglycolic acids, and silicone. Synthetic extracellular matrices are described in Putnam and Mooney, Nat Med 1996 July; 2(7):824–6.

Matrices useful in the compositions and methods of this invention may be pre-formed. or they may be formed in situ, for example, by polymerizing compounds and compositions such as fibrinogen to form a fibrin matrix. Matrices that may be pre-formed include those made from the following components, or various mixtures of the following components: collagen, collagen analogs or collagen mimics (e.g., collagen sponges and collagen fleece), chemically modified collagen, gelatin beads or sponges, gel-forming or composite substances comprising a biocompatible matrix material that will allow cells to populate the matrix, and collagen complexed with other compounds to enhance collagen's ability to polymerize, maintain its structure, or resist degradation. See, e.g., U.S. Pat. Nos. 5,830,492; 5,824,331; 5,834,005; and 5,922,339.

In addition to fibrin gels, Matrigel, alginate, agarose, and biological-molecule-impregnated polyester have been used as matrices to enhance angiogenesis. See Fournier and Doillon, Biomaterials 17:1659–65 (1996). Zimrin AB et al., Biochem Biophys Res Commun 1995 August 15; 213(2):630–8, noted that there were some differences between endothelial cells cultured in the presence of fibrin versus those cultured in Matrigel.

U.S. Pat. No. 5,830,504 discloses an artificial bioactive matrix comprising cooperative combinations of ligands within a matrix.

Kim B S et al., Biotechnol Bioeng Jan. 5, 1998; 57(1):46–54, describe the use of polyglycolic acid as an extracellular matrix.

Changes in extracellular matrix structure and composition can have important regulatory effects on cell behavior. For example, Kanzawa et al., Ann Plast Surg 1993 March; 30(3): 244–51, examined angiogenesis in a three-dimensional model in vitro, using HUVECs cultured in a collagen gel. An abundant, capillary-like network with a lumen structure was seen histologically, forming at a collagen density less than 0.15% for either type I or type III collagen. At the same density, type III collagen induced a capillary-like network with HUVECs at an earlier stage of culture than did type I collagen. Thus, both collagen density and type can influence angiogenesis.

Endothelial growth medium is a serum-free medium that supports the growth and maintenance of vascular endothelial cells. See, e.g., Gorfien et al. (1993) Exp. Cell Res. 206, 291; and Gorfien et al. (1992) Focus 14: 14. The high levels of serum supplementation that are often used in endothelial cell culture may create problems in experimental design or in interpretation of results.

Gorman L et al., Nutrition 1996 April; 12(4):266–70, further refined the growth requirements of endothelial cells. These authors reported that M199 medium that is deficient in amino acids but supplemented with glutamine was superior to M199 complete medium (medium 199 (Gibco BRL, Grand Island, N.Y.)).

U.S. Pat. Nos. 6,139,574 and 6,176,874 disclose solid free-form (e.g., polymeric) fabrication methods for manufacturing devices for tissue regeneration, in a matrix having a network of lumens said to be functionally equivalent to the naturally occurring vasculature of tissue, which can be lined with endothelial cells and coupled to blood vessels at the time of implantation.

Published international application WO 95/23968 discloses a method for obtaining angiogenesis by culturing a blood vessel fragment with a physiological gel and nutrients. The physiological gel was said to preferably be fibrin, collagen, Matrigel, or similar.

"Cell treatment could help doctors make old hearts young again," internet article available at http://www.cnn.com/2000/HEALTH/11/12/heart.repair/index.html (November 2000) is an account in the popular press of treating damaged hearts by injecting isolating skeletal myoblasts around the area of a scar on the heart tissue. Similar approaches using marrow stromal cells and circulating immature endothelial cells were also mentioned.

No prior reports are known of angiogenesis assays for tumors or other tissue in which the intact three-dimensional structure of the tissue is maintained during the assay—as opposed to, for example, reports of an assay conducted on an isolated artery or vein.

No prior reports are known in which angiogenesis has been promoted in three-dimensional tissues ex vivo prior to transplantation.

We have discovered an in vitro tissue angiogenesis and vasculogenesis system that allows the outgrowth of microvessels from a three-dimensional tissue fragment implanted in a matrix. The matrix may, for example, be a fibrin- or collagen-based matrix fed by a growth medium, for example, a mixture of tissue culture medium, serum, or a layer of serum-free medium with defined growth factors. This system, which may be used with human or other mammalian or animal tissues, maybe used in assaying tumor angiogenic potential, or in promoting angiogenesis in other tissues, e.g., promoting angiogenesis prior to transplantation of a tissue. The angiogenic potential of a tissue can be determined by measuring the growth of microvessels into the matrix. The system is based on endogenous angiogenesis, vasculogenesis, neovascularization, or tissue perfusion, independent of tumor angiogenesis or other tissue angiogenesis. By contrast, tumor angiogenesis per se results from the formation of patterned networks of interconnected loops of extracellular matrix through which tumor perfusion may occur. The three-dimensional structure of the tumor or other tissue is maintained in the matrix, including its blood vessels, supportive stromal elements such as fibroblasts, and neural and endothelial cells. In another aspect, the method allows for the proliferation of a tissue specimen, thus increasing the mass of cells available for subsequent transplant; and the method also provides for the proliferation of blood vessels from the tissue mass, thus enhancing the chance of successful engraftment. The mass of the tissue to be transplanted is preferably increased by at least about 25%, more preferably by at least about 50%, most preferably by at least about 100%.

Unless otherwise clearly indicated by context, the appearance of new vessels in the novel system, whether by angiogenesis or vasculogenesis, is considered as a measure of the angiogenic potential of a tumor or other tissue. Classification as "angiogenesis," "vasculogenesis," or "neovascularization" may help promote understanding, but should not be interpreted to limit the scope of the present invention. Moreover, for the purposes of the present specification and claims, unless otherwise clearly indicated by context, the term "angiogenesis" should be interpreted also to include the processes of vasculogenesis and neovascularization.

The novel system displays several unique and surprising characteristics that are not found in any known prior tissue angiogenesis model. Intact tissue architecture is maintained, including supportive stromal elements (e.g., fibroblasts), neural tissues, and endothelial tissues. The inclusion of such elements is important, as the presence of these tissues and of the supporting fibrin matrix better provide the framework required for angiogenesis and growth of tumors or other tissues. Vessel growth rate typically exceeds the rate of tissue growth, meaning that the growth rate of angiogenic vessels maybe measured without interference from tissue growth. The ability to independently and accurately measure the growth of angiogenic vessels is particularly surprising, because no known prior model has provided this important capability. The differential growth pattern of tissue cells and angiogenic vessels in a fibrin gel matrix separates the angiogenic vessels and the tissue stroma into independently observable regions of interest (vessel and tissue compartments). The compartmental structure of the novel system allows the measurement of differential effects of various anti-tumor or tissue stimulatory therapies on tissue and angiogenic vessel components.

The present invention may be used to observe angiogenesis in any type of solid tumor, or to promote angiogenesis in any type of normal, vascularized tissue. If desired, results may be expressed in a semi-quantitative or quantitative manner; quantification may be conducted, for example, by direct examination, computer-assisted image analysis, or measurements of surrogate indicators of the creation of perfusion channels. Examples of such surrogate indicators include tritiated-thymidine uptake, gene up regulation, and $^{125}$I-bromodeoxyuridine uptake.

Methods of cell culture, gel formation, vessel quantitation, and matrix preparation are well known in the art. Thus, most methods of cell culture or gel formation that will support growth of cells embedded within a matrix may be used to practice the present invention, including by way of example those described in the present application. Moreover, most matrices capable of supporting angiogenesis may be used to practice the present invention, including by way of example those described in the present application. Also, any method of vessel quantitation, including but not limited to those described in the present specification, may be used to practice the invention.

Test compounds, angiogenesis factors, or sera are preferably layered over or incorporated into the feeding layer in an appropriate concentration. The compounds or sera then diffuse into the fibrin matrix to produce effects on the tissue fragment and its sprouting angiogenic vessels.

Evaluation of Neovessel Initiation.

The initiation fraction may be computed by counting the number of wells that develop an angiogenic response, and dividing by the total number of wells plated.

Angiogenesis Initiation Rate.

The initiation rate equals the slope of the curve of a plot of the fraction of angiogenesis initiation in culture against time.

Evaluation of Neovessel Proliferation/Promotion.

For subjective scoring, the discs are divided into four quadrants and rated on a 0–4 scale for the amount of angiogenic growth. Using a 0–4 rating scale in each of four quadrants, a total score of 0–16 may be determined for each well. If desired, a more objective measurement may be obtained, for example, by using optical microscopy and digital image analysis to measure the total surface area of angiogenic sprouting. By measuring total surface area as a function of time, the rate of change may be determined.

Viability Measurements. Cellular viability may be evaluated using any of various methods known in the art. A convenient method is a colorimetric assay such as the MTT assay (Promega, Madison, Wis.). This assay is based on the cellular conversion of a tetrazolium salt into a blue formazan product. The MTT assay can be performed at the end of a specified time period on both the tissue fragment and on angiogenic sprouts. This assay can be used, for example, to compare drug/sera-treated and untreated wells.

Proliferation Measurements.

Any of various methods known to the art may be used to measure proliferation of cells. For example, uptake of non-specific tracers such as $^3$H-thymidine or $^{125}$I-UDR, which incorporate only into actively dividing cells, may be used to compare uptakes in treated wells versus untreated wells. Use of specific receptor-mediated tags can also be used to assess tissue-versus-vessel uptake in treated and untreated wells. Statistically significant differences in uptake are attributed to effects of the drug, serum, or other treatment.

Tumor and Other Tissue Sources.

Monolayer cell lines, solid tumor fragments, or other tissues may be harvested from or grown in a suitable host animal. A suitable host for many experimental purposes is the nude mouse. Tumors, for example, are harvested upon reaching a size of 1–2 cm, which is sufficient to provide an adequate number of tumor discs. For clinical purposes, fresh surgical specimens may be used to assess the angiogenic potential of a particular tumor or other tissue. Exposing a cut surface within the tumor or other tissue, i.e., exposing cut blood vessels, is believed to enhance the tissue's angiogenic response by inducing hypoxia in the transected vessel edges.

Assays.

The novel system may be used in various assays to test the effects of different agents on angiogenesis. Examples of such agents include growth factors, growth factor inhibitors, serum (including autologous serum), chemotherapeutic agents, external beam radiation, in-situ radiation therapy (such as that delivered via radiopharmaceutical targeting compounds, for example radiolabeled somatostatin, monoclonal antibodies, and peptides), growth factors, growth factor inhibitors, steroid and peptide hormones or their analogs, and chemotherapeutic agents.

Monolayers of various tumor cells lines can be placed into or onto a solid/semi-solid feeder layer to test the effects on angiogenesis of mediators released from the cells.

In Vitro Metabolic Manipulations.

The tissue-specific metabolism of different soluble substances may be evaluated by implanting cells, for example hepatocyte clusters or liver fragments, into the solid/semi-solid feeder layer. The effects of soluble factors in circulating blood may be evaluated by replacing the liquid feeder layer with serum, including autologous serum from the same patient.

Non-Oncological Applications.

In addition to evaluating responses in tumors, this invention allows the evaluation or the promotion of angiogenic responses in other tissues or organs undergoing physiologic or pathophysiologic changes. Such other applications include, for example, the evaluation of embryologic tissues, the promotion of angiogenesis in wounds, in cardiac muscle; or conversely the evaluation of the inhibition of angiogenesis in inflamed tissues of rheumatic disorders, or in skin conditions such as psoriasis. Other applications include the induction of angiogenesis in a tissue transplant, including an autologous transplant; diseases such as parathyroid reimplantation in the forearm following total parathyroidectomy, or reimplantation of pituitary, adrenal, pancreatic, other endocrine tissues, or other peptide- or amine-producing tissues. The inhibitors and stimulators of angiogenesis in any tissue may be studied using an assay in accordance with the present invention. Tissue may be allowed to grow in assay conditions until the host tissue proliferation increases significantly above the mass of tissue originally implanted in the system.

In Vivo Systemic Assays Using the Present Invention.

The present invention maybe used in conjunction with an in vivo systemic assay. Tumor growth is initiated in a suitable host such as the nude mouse or rat; the tumors are allowed to grow to 1–2 cm; and the tumors are then challenged systemically with the test compound or radiation treatment of interest. Following treatment, the animal is sacrificed and a tumor is harvested. A tumor harvested prior to the systemic test serves as a control. The tumors are both processed as per the 3DTAM protocol (S. Gulec et al., "A new in vitro angiogenesis assay with spatially intact human tumor architecture. The 3D tumor angiogenesis model (3DTAM), preprint 2001). Both sets of tumor fragments are evaluated for their angiogenic response. This approach allows one to assess the effects of in vivo therapy in the presence of biologic variables that affect drug pharmacokinetics, such as liver metabolism and renal excretion, as well as humoral interactions at the plasma or tissue level.

Multi-compartment Techniques.

Multiple compounds or radiation treatments can be evaluated simultaneously with multiple wells, separated from one another by dialysis membranes. Multi-compartment procedures can also be conducted with compartments or wells comprising a non-toxic, water-soluble or water-insoluble gel. Such gels include, for example, collagen, other collagen-based materials as previous discussed, agarose, agar, alginate, silica, or protein-based gels such as gelatin. The wells are loaded with fibrin, or with a soft gel containing tissue samples. In this embodiment, the compartments or wells may optionally be sealed, for example with a layer of agarose, before the wells are filled. Adjacent wells may be used for sera, tumor, or tissue to provide comparative data. A multi-compartment system separated by semipermeable membranes or gels may be used to evaluate the ability of a tumor, serum, or other factor to induce a directional angiogenic response. Optionally, one may harvest all or a portion of the gel separating different wells. The harvested portions may then be assayed for specific diffusible substances responsible for inducing a directional angiogenic response.

Advantages of the Novel System

The invention allows a tumor or other tissue to induce an angiogenic response while maintaining an intact three-dimensional architecture.

The present invention offers several advantages. It allows the evaluation of a tumor or other tissue's angiogenic response while maintaining an intact three-dimensional architecture. Tumor (or other tissue) compartments maybe evaluated simultaneously or separately. The novel system allows the evaluation of drugs that require activation in vivo and drugs that are active ex vivo. One advantage of this invention is that it may be used to provide a functional (as opposed to histological) angiogenic index. A functional angiogenic index may help to reveal tumors with a poor prognosis due to a high functional angiogenic index, even though they may have a low histological angiogenic index. A disparity between functional and histological angiogenic indices may occur if circulating anti-angiogenic substances (such as angiostatin/endostatin) mask the angiogenic potential of a tumor. Culturing tumors in a serum-free environment may better "unmask" angiogenic suppressors or stimulators, and thus better reveal their true angiogenic potential. In lieu of a serum-free environment, a low serum environment (e.g., less than about 20% or less than about 10% serum) may be used. This may demonstrate that removal or de-bulking of tumors that secrete a suppressor is not warranted and may be harmful.

Conversely, using this system in the presence of high serum levels (greater than about 50% serum) may unmask angiogenesis suppressors that are present in some serum types, such as those from nude mice implanted with Lewis lung carcinoma.

The invention may also be used to develop prognostic tests for a patient's resistance or susceptibility to the future development of malignancy or angiogenesis-related diseases.

An important aspect of the invention is its use in ex vivo angiogenesis to develop a blood supply in a tissue to be engrafted, thus decreasing the time needed for adequate microcirculation to develop after implantation. This method also promotes the proliferation of tissue, which may increase the cell population available to engraft subsequently. Such cell population increase may be desirable for implantation of various tissues, for example endocrine tissue (e.g., thyroid, adrenal glands, pancreas, pituitary, parathyroid), muscle tissues (e.g., cardiac or skeletal muscle), kidney, liver, skin, prostate, retina, and other tissues.

The invention may also be used to evaluate the up or down regulation of a specific gene by a tumor or tissue, thus allowing treatments to be based on gene expression.

EXAMPLES

As initial examples, we studied receptor mediated cytotoxic effects of various radiolabeled somatostatin analogs.

This initial study observed significant in vitro cytotoxic effects on human tumors and their angiogenic vessels by somatostatin analogs labeled with $^{111}$In, $^{125}$I, or both.

We used the novel compartmental angiogenesis system to study the differential effects of somatostatin receptor subtype 2 ("sst-2") mediated, in situ radiation therapy on tumors and their angiogenic vessels in a way that could not have been accomplished with prior angiogenesis models. The most dramatic results were obtained with IMR-32 (human neuroblastoma) tumors, in which both the tumor and the vascular compartments expressed sst-2. Tumor dissolution and angiogenic vessel disruption were seen in all fragments that were treated with a radiolabeled somatostatin analog. Conversely, we observed no effect of radiolabeled somatostatin analogs on the MDA (human breast carcinoma) tumor fragments. Watson, J. C. et al., Surgery August; 122(2): 508–13 (1997) demonstrated similar differences in the cytotoxicity of somatostatin analogs labeled with Auger emitters in tumor cell monolayer cultures.

Somatostatin analogs containing an Auger electron-emitting label provided an excellent test of the invention. Auger electron treatment represents true in situ radiation therapy, in which radiation is delivered to a target following the specific high affinity binding of a radiolabeled ligand (e.g., a somatostatin analog) to its receptor (e.g., a somatostatin receptor). Auger electrons emitted by radioisotopes such as $^{111}$In or $^{125}$I have a very short range (on the order of 50 Å), and are therefore only effective if the radioisotope can be delivered intracellularly, preferably to the nucleus itself. The use of Auger electron-emitting, targeted radiopharmaceuticals limits collateral radiation damage to normal cells by limiting cytotoxicity to those cells that bind and internalize the radioligand. Moreover, since the somatostatin receptor sst-2 is uniquely over-expressed in angiogenic blood vessels, labeled somatostatin analogs will bind only to angiogenic blood vessels, but not to their normal counterparts.

We chose the somatostatin analogs $^{111}$In-pentetreotide (Mallinckrodt Medical, St. Louis, Mo.), JIC2DL, and DTPA-JIC2DL. (For the latter two compounds, see D. Coy, W. Murphy, E. Woltering, J. Fuselier, and G. Drouant, "Hydrophilic Somatostatin Analogs," U.S. patent application Ser. No. 09/196,259, filed Nov. 19, 1998.) The analogs were labeled with either $^{111}$In or $^{125}$I, or in some cases were dually labeled with both isotopes. JIC2DL has a sub-nanomolar binding affinity to the somatostatin receptor sst-2 (personal communication, David Coy, Tulane University, New Orleans, La.). JIC2DL can be iodinated on its two-tyrosine residues, while DTPA-JIC2DL can be labeled with $^{111}$In, $^{125}$I, or both.

We hypothesized that tumor xenograft explants expressing the sst-2 receptor would show cytotoxic changes when treated with radiolabeled somatostatin analogs, while those without sst-2 would not. We also hypothesized that treatment with radiolabeled somatostatin analogs would inhibit angiogenic blood vessel growth, independent of the tumor's sst-2 status.

We cultured two human carcinoma cell lines obtained from the American Tissue Culture Collection (ATCC). One cell line (IMR-32) expressed the sst-2 receptor and the other (MDA-MB-231 did not). We implanted these cell lines into nude mice to create human tumor xenografts. Subsequently we harvested the xenografts and embedded tumor fragments in fibrin gel matrixes. These tumor-containing gels were treated with radiolabeled somatostatin analogs to determine whether these compounds would destroy tumor cells or angiogenic blood vessels.

We demonstrated that the IMR-32 human neuroblastoma cell line expressed sst-2 as expected from its neuroendocrine differentiation, while the MDA-MB-231 human breast adenocarcinoma cells did not express sst-2. Angiogenic vessels also express sst-2, while other blood vessels do not. We tested the following two compartment pairs with these cell lines: (1) sst-2 (+) tumor, sst-2 (+) neovessels; and (2) sst-2 (−) tumor, sst-2 (+) neovessels.

The human breast carcinoma cell line, MDA-MB-231, was maintained in Lebowitz's L-15 medium (Life Technologies Inc, Grand Island, N.Y.), supplemented with 10% fetal bovine serum (FBS) (Life Technologies Inc, Grand Island, N.Y.). The human neuroblastoma cell line, IMR-32, was maintained in Minimum Essential Medium (Life Technologies, Inc, Grand Island, N.Y.), supplemented with 15% FBS, non-essential amino acids (Life Technologies Inc, Grand Island, N.Y.), L-glutamine (Cellgro, Va.), and antibiotics. Cells were harvested at subconfluence and resuspended in Hank's balanced salt solution (Life Technologies Inc, Grand Island, N.Y.).

While the initial examples described here report results obtained with fresh human surgical tumors or with tumors derived from tumor cell lines, the same general technique will also work to promote angiogenesis ex vivo in tissue explants intended for transplantation. Such tissues may, for example, be autologous, or they may be obtained during harvest from operative specimens, or brain dead donors—all in accordance with applicable statutes, regulations, and Institutional Review Board procedures. The tissues will often proliferate in culture in parallel with angiogenesis, further enhancing the usefulness of the tissue in transplantation. The ability to transplant intact tissues with preformed angiogenic vessels in this manner should provide substantial clinical benefits as compared to the infusion of individual cells, or the transplant of tissue that has not been allowed to develop an angiogenic response.

Nude Mice and Creation of Human Tumor Xenografts.

All animal experiments reported in this specification were approved by the Louisiana State University Health Sciences Center animal care committee. BALB/c Harlan Sprague Dawley nude mice (Indianapolis, Ind.) were injected with $1.5 \times 10^7$ cells subcutaneously in both flank regions. The mice invariably grew solid tumors at the site of injection over a period of 4–6 weeks. The tumors were allowed to reach a size of 1.5–2 cm. (Continued growth to larger tumor sizes would often be accompanied by central tumor necrosis.) Tumors were harvested using a sterile technique under inhalation anesthesia with methoxyflurane. The mice were euthanized immediately after tumor harvest.

Preparation of Tumor Fragments.

Fresh tumors were processed immediately after harvesting. Tumor fragments 2 mm diameter and 1 mm thick were prepared, and then embedded in a fibrin gel. The fibrin gels were prepared in 96 well-plates using a specific tumor supporting medium as described below.

Preparation of the Tissue Supporting Medium.

A serum-free, basic growth medium comprising a balanced salt solution, an antibiotic-antifungal solution, and an endothelial growth medium was buffered to a pH of 7.4. Specifically, 9.5 g of medium 199 (Gibco BRL, Grand Island, N.Y.) was dissolved in 980 mL deionized $H_2O$. 10 mL of antibiotic-antimycotic solution (Gibco BRL, Grand Island, N.Y.) containing 10,000 U of penicillin base, 10,000 U of streptomycin base and 25 $\mu$g of Amphotericin B was added. The pH was then adjusted by adding 2.2 g of Na $HCO_3$ (EM Science, Gibbston, N.J.), and was further titrated with 1N NaOH if needed to reach a pH of 7.4. This solution was mixed with endothelial growth medium (EGM) (Gibco BRL, Grand Island, N.Y.) in a 3:1 ratio, and was sterilized by passing it through a 0.22-micron filter.

Preparation of Fibrin Matrix Components for Tumor Fragment Embedding.

A pro-coagulation solution was prepared by dissolving fibrinogen (0.12 g) (Sigma, St. Louis, Mo.) and 0.2 g of ε-amino caproic acid in 40 mL endothelial growth medium. Human thrombin (2 μl) (Sigma, St. Louis, Mo.) was placed in the bottom of each well of a 96 well plate. Endothelial growth medium is a serum-free medium designed for the growth and maintenance of vascular endothelial cells. See Gorfien et al. (1993) Exp. Cell Res. 206: 291; and Gorfien et al. (1992) Focus 14: 14.

Final Assembly of the Fibrin Matrix Tumor System, and Maintenance of the Well-Plates.

One tumor disc was placed in the center of each thrombin-treated well. 0.2 mL procoagulation solution was carefully layered over the tumor fragments in each of the wells. Fibrin clot formation took place within 20–30 minutes at 37° C. The plates were kept at 37° C. in a 5% CO2/95% air humidified atmosphere.

Radiolabeled Somatostatin Analogs, Treatment and Evaluation Protocol. The radiolabeled somatostatin analogs used in the experiments with the IMR-32 tumor line were (1) $^{111}$In pentetreotide (Mallinckrodt Medical St. Louis, Mo.); (2) $^{111}$In-DTPA JIC2DL; (3) $^{125}$I-JIC 2DL and (4) $^{111}$In- and $^{125}$I-DTPA JIC2DL. Support medium containing the radiopharmaceutical was added over the fibrin clots in the well plates bearing the tumor fragments, at 100 μCi/well. Concentrations for the $^{111}$In-labeled analogs and the $^{125}$I-labeled analogs were $7.2 \times 10^{-9}$ M and $3.9 \times 10^{-8}$ M, respectively. Treatments were administered on the first day of tumor implantation. Each treatment group contained 30 tumor fragments. IMR-32 tumor fragments were treated with all 4 radiopharmaceuticals tested (i.e., n=(30/treatment group)×4 groups=120 total). $^{111}$In-DTPA JIC2DL was the only radiolabeled somatostatin analog used in the experiments with the MDA-MB-231 tumor line (n=30). Control groups were given the support medium only (n=30 for each of the two tumor types). Capillary sprouting was monitored visually for 14 days.

The percentage of wells in which new angiogenic vessel growth initiated was observed. For subjective angiogenic scoring, the discs were divided into four quadrants and rated on a 0–4 scale for the amount of angiogenic growth. Using this 0–4 rating scale in each of four quadrants, a total score of 0–16 was given for each tumor fragment. The mean ± standard deviation of the angiogenic score for each treatment group was calculated. Means for control and treatment groups were compared for statistical significance (P<0.05) using the two-tailed Student t-test.

RESULTS

Angiogenic Initiation.

The angiogenic initiation fraction for all cultures was similar, regardless of tissue type or treatment. Untreated AMR fragments (24/30; 80%) and untreated MDA tumor fragments (25/30; 83%) demonstrated angiogenic growth. The initiation fraction in $^{111}$In-DTPA-JIC2DL treated IMR and MDA tumor fragments were 25/30 (83%) and 24/30 (80%) respectively. The differences in initiation fractions of treated and untreated tumor fragments in both groups were not statistically significant. The initiation fractions for the IMR tumor fragments treated with the other radiopharmaceuticals were not significantly different from control, ranging from 21/30 (70%) to 25/30 (83%).

Angiogenic Response.

The endpoints used to evaluate the compartmental tumor angiogenesis system included the response of the tumor (regression/disintegration) and the angiogenic response. The angiogenic response endpoints comprised the total angiogenic score, the full angiogenic response fraction, the angiogenic inhibition pattern, primary-secondary failure, and architectural disruption. Angiogenic scores were calculated for each group of tumor fragments on day 14 using a visual rating system. Fragments that did not show angiogenic initiation were excluded from this portion of the analysis. Mean angiogenic scores for the control groups of IMR and MDA tumor fragments were similar (11.9±3.3 and 12.4±3.9, respectively). In the treated IMR lines, groups were observed with severe architectural disruption associated with tumor necrosis. No comparable scoring, therefore, was possible for this treatment. In the treated MDA group, the mean angiogenic score was 6.4±2.9. This score was significantly different from the mean angiogenic score of the MDA control group (12.4±3.9)(p<0.0001). 20/24 (83%) of the tumor fragments in the MDA treatment group showed architectural disruption and evidence of vessel destruction.

Tumor Response.

All tumor fragments in the control groups for both tumor cell lines remained intact on day 14. In the treated IMR groups, all tumor fragments showed degenerative changes ranging from vacuolization to nearly complete tumor lysis. No significant differences were seen among the anti-tumor effects of the 4 different radiopharmaceuticals. In the treated MDA group, all tumor fragments remained intact, with no evidence of cytotoxic changes.

The most dramatic results were seen with the IMR-32 tumors, in which both the tumor and the vascular compartments expressed sst-2. Tumor dissociation and angiogenic vessel degradation were seen in all fragments that received the experimental treatment. Conversely, no effect was seen on the MDA tumor fragments. However, angiotoxicity was seen in 92% of the experimental MDA fragments. Sparing of the MDA (sst-2 negative) tumor compartment from the effects of the in situ radiation was strong evidence of the highly selective nature of the Auger emitter treatment.

Definition

Any biological system will, in a literal sense, be three-dimensional. However, as used in the specification and claims, a tissue or tissue fragment is considered to be "three-dimensional" if it has multiple layers of cells comprising blood vessels and other cells of the tissue, and if the architecture of the tissue or tissue fragment (including, for example, the blood vessels, supportive stromal elements such as fibroblasts, neural and endothelial cells) is substantially intact and has not been disrupted as compared to the comparable tissue in vivo. As examples, a tumor, tumor sample, other tissue, or other tissue sample is considered "three-dimensional" within the scope of this definition if its structure has not been disrupted. It may be sliced or reduced in thickness, so long as multiple layers of cells are retained, and so long as the relative structure and relation of blood vessels and other cells to one another is maintained.

As examples, the following would not be considered "three-dimensional" within the scope of the above definition: an isolated vein; an isolated artery; isolated cells from a disrupted tumor or other tissue; or an agglomerations of cells grown in culture—even an agglomeration that has substantial thickness and is "three-dimensional" in the ordinary sense—if the agglomeration lacks the architecture of the comparable tissue in vivo—such as an agglomeration of tumor cells grown in culture without any vascularization.

The complete disclosures of all references cited in this specification are hereby incorporated by reference. In the event of an otherwise irreconcilable conflict, however, the present specification shall control. Also incorporated by reference are the complete disclosures of the following unpublished papers, none of which is prior art to the present invention: S. Gulec et al., "Antitumor and antiangiogenic effects of somatostatin receptor-targeted in situ radiation with $^{111}$In-DTPA-JIC2DL," *J. Surg. Res.*, vol. 97, pp. 131–137(2001); and S. Gulec et al., "Anti-treatment with somatostatin receptor-mediated in situ radiation," *American Surgeon* (in press, 2001); S. Gulec et al., "A new in vitro angiogenesis assay with spatially intact human tumor architecture. The 3D tumor angiogenesis model (3DTAM) (preprint 2001). Also incorporated by reference is the complete disclosure of the priority provisional application No. 60/nnn,nnn (which is a conversion of nonprovisional application Ser. No. 09/580,894), filed May 30, 2000.

We claim:

1. A method for assaying the angiogenic potential of a particular tumor in a mammal; said method comprising the steps of:
   (a) embedding a three-dimensional tissue sample in a matrix, wherein the tissue sample is taken from a particular tumor in a mammal; wherein the tissue sample has at least one cut surface exposing blood vessels; wherein the three-dimensional tissue sample comprises multiple layers of cells comprising blood vessels, supportive stromal elements, neural cells, and endothelial cells; wherein the architecture of the tissue sample is substantially intact and has not been disrupted as compared to that of comparable tissue in vivo; and wherein the three-dimensional tissue sample does not consist of an isolated artery or an isolated vein;
   (b) supplying to the embedded tissue sample a medium that supports the growth of the tissue sample;
   (c) incubating the embedded tissue sample in the medium for a time sufficient to allow any angiogenic vessels to grow into the matrix surrounding the tissue sample; and
   (d) observing or measuring any angiogenic vessels that grow into the matrix surrounding the tissue sample;
whereby:
the growth or any angiogenic vessels into the matrix is a measure of the angiogenic potential of the particular tumor from which the tissue sample was taken.

2. A method as recited in claim 1, wherein the medium comprises a serum-free medium that supports the growth of the tissue sample; wherein the medium contains substantially no exogenous angiogenesis-enhancing factors and substantially no exogenous angiogenesis-suppressing factors.

3. A method as recited in claim 1, wherein the medium comprises serum.

4. A method as recited in claim 1, wherein the medium comprises an angiogenesis-enhancing factor.

5. A method as recited in claim 4, wherein the angiogenesis-enhancing factor is selected from the group consisting of platelet-derived growth factor, vascular endothelial growth factor, epidermal growth factor, fibroblast growth factor, and transforming growth factor β.

6. A method as recited in claim 1, wherein the matrix comprises fibrin.

7. A method as recited in claim 1, wherein the matrix comprises collagen.

8. A method as recited in claim 1, wherein the matrix comprises gelatin.

9. A method as recited in claim 1, wherein the matrix comprises agarose, agar, alginate, or silica gel.

10. A method as recited in claim 1, wherein the matrix comprises Matrigel™ matrix.

11. A method as recited in claim 1, additionally comprising the step of supplying a factor to the embedded tissue sample, and measuring the difference in angiogenesis for the tissue sample as compared to the angiogenesis of an otherwise identical and otherwise identically-treated control tissue sample that is not supplied with the factor; whereby the difference in observed angiogenesis is a measure of the angiogenic enhancement or angiogenic suppression characteristics of the supplied factor.

12. A method as recited in claim 1, wherein said method additionally comprises the step of supplying an angiogenic suppression factor to the tissue sample, and measuring the difference in angiogenesis for the tissue sample as compared to the angiogenesis of an otherwise identical and otherwise identically-treated control tissue sample that is not supplied with the factor; whereby the measured difference in angiogenesis between the samples is a measure of the angiogenic suppression characteristics of the supplied factor against the tumor from which the sample was taken.

13. A method as recited in claim 1, wherein said method additionally comprises the step of supplying an angiogenic stimulation factor to the embedded tissue sample, and measuring the difference in angiogenesis for the tissue sample as compared to the angiogenesis of an otherwise identical and otherwise identically-treated control tissue sample that is not supplied with the factor; whereby the measured difference in angiogenesis between the samples is a measure of the angiogenic stimulation characteristics of the supplied factor for the tissue from which the sample was taken.

* * * * *